(12) United States Patent
Manzo

(10) Patent No.: US 9,937,074 B2
(45) Date of Patent: Apr. 10, 2018

(54) IONTOPHORETIC CONTACT LENS

(71) Applicant: Eyegate Pharmaceuticals, Inc., Waltham, MA (US)

(72) Inventor: Michael Manzo, Beverly, MA (US)

(73) Assignee: EyeGate Pharmaceuticals, Inc., Waltham, MA (US)

( * ) Notice: Subject to any disclaimer, the term of this patent is extended or adjusted under 35 U.S.C. 154(b) by 5 days.

(21) Appl. No.: 15/004,867

(22) Filed: Jan. 22, 2016

(65) Prior Publication Data
US 2016/0213514 A1 Jul. 28, 2016

Related U.S. Application Data

(60) Provisional application No. 62/106,578, filed on Jan. 22, 2015.

(51) Int. Cl.
| | | |
|---|---|---|
| *A61N 1/30* | (2006.01) | |
| *A61F 9/00* | (2006.01) | |
| *G02C 7/04* | (2006.01) | |
| *A61K 9/00* | (2006.01) | |
| *A61N 1/04* | (2006.01) | |

(52) U.S. Cl.
CPC .......... *A61F 9/0017* (2013.01); *A61K 9/0009* (2013.01); *A61K 9/0048* (2013.01); *A61N 1/0428* (2013.01); *A61N 1/30* (2013.01); *G02C 7/04* (2013.01); *A61N 1/044* (2013.01)

(58) Field of Classification Search
CPC ....... A61F 9/0017; A61N 1/30; A61N 1/0428; A61N 1/044; A61N 1/08; G02C 7/04; A61K 9/0009; A61K 9/0048

USPC .......................................................... 604/20
See application file for complete search history.

(56) References Cited

U.S. PATENT DOCUMENTS

| 4,915,685 A | 4/1990 | Petelenz et al. |
| 6,154,671 A | 11/2000 | Parel et al. |
| 6,319,240 B1 | 11/2001 | Beck |
| (Continued) | | |

FOREIGN PATENT DOCUMENTS

| CN | 203389001 | 1/2014 |
| WO | 2003030989 A2 | 4/2003 |
| (Continued) | | |

OTHER PUBLICATIONS

International Search Report and Written Opinion from related PCT Application No. PCT/US16/14636 dated May 12, 2016.
(Continued)

*Primary Examiner* — Jason Flick
(74) *Attorney, Agent, or Firm* — Burns & Levinson, LLP; Joseph M. Maraia

(57) ABSTRACT

Contact lenses are provided for ocular iontophoretic therapy. Implementations include a reservoir adapted to contain a charged therapeutic compound, a current source providing iontophoretic current to the charged therapeutic composition to affect delivery of the charged therapeutic composition into an eyeball, and a sensing circuit controlling the current source to maintain a selected pH range of the charged therapeutic composition. Alternate embodiments include active, sacrificial electrodes for generating ions sufficient to provide electromotive repulsive force to the charged compound to effect transport into ocular tissue.

12 Claims, 5 Drawing Sheets

(56) References Cited

U.S. PATENT DOCUMENTS

| | | |
|---|---|---|
| 6,539,251 B2 | 3/2003 | Beck et al. |
| 6,544,193 B2 | 4/2003 | Abreu |
| 6,579,276 B2 | 6/2003 | Lloyd et al. |
| 6,678,554 B1 | 1/2004 | Sun et al. |
| 6,697,668 B2 | 2/2004 | Parkinson et al. |
| 7,164,943 B2 | 1/2007 | Roy |
| 7,346,389 B1 | 3/2008 | Newsome |
| 7,398,121 B2 | 7/2008 | Matsumura et al. |
| 7,809,417 B2 | 10/2010 | Abreu |
| 7,848,800 B2 | 12/2010 | Behar-Cohen et al. |
| 8,480,638 B2 | 7/2013 | Tuitupou et al. |
| 8,611,994 B2 | 12/2013 | Roy |
| 8,755,880 B2 | 6/2014 | Higuchi et al. |
| 8,971,978 B2 | 3/2015 | Ho et al. |
| 9,101,309 B1 | 8/2015 | Liu et al. |
| 2002/0107508 A1 | 8/2002 | Burnett |
| 2003/0208235 A1 | 11/2003 | Miller et al. |
| 2007/0074590 A1 | 4/2007 | Smith |
| 2007/0083185 A1 | 4/2007 | Carter |
| 2007/0299386 A1 | 12/2007 | Peyman |
| 2008/0027371 A1 | 1/2008 | Higuchi et al. |
| 2008/0131483 A1 | 6/2008 | Abdulrazik |
| 2009/0093780 A1* | 4/2009 | Tuitupou .............. A61F 9/0017 604/294 |
| 2010/0028406 A1 | 2/2010 | Kalia et al. |
| 2010/0040669 A1 | 2/2010 | Higuchi |
| 2010/0209515 A1 | 8/2010 | Chantalat et al. |
| 2011/0028807 A1 | 2/2011 | Abreu |
| 2011/0301526 A1 | 12/2011 | Moslemy et al. |
| 2013/0178821 A1 | 7/2013 | Foschini et al. |
| 2013/0194540 A1 | 8/2013 | Pugh et al. |
| 2014/0005514 A1* | 1/2014 | Pugh .................... A61F 9/0017 600/383 |
| 2014/0107025 A1 | 4/2014 | Wirostko |
| 2014/0190839 A1 | 7/2014 | Liu |
| 2015/0164321 A1 | 6/2015 | Weibel et al. |
| 2015/0188197 A1 | 7/2015 | Liu et al. |
| 2015/0305929 A1 | 10/2015 | Goldberg et al. |
| 2015/0362751 A1 | 12/2015 | Biederman |

FOREIGN PATENT DOCUMENTS

| | | |
|---|---|---|
| WO | 2003043689 A1 | 5/2003 |
| WO | 2006072887 | 7/2006 |
| WO | 2008125908 A2 | 10/2008 |
| WO | 2012162459 A1 | 11/2012 |

OTHER PUBLICATIONS

Costa et al., "Development of Therapeutic Contact Lenses using a Supercritical Solvent Impregnation Method" The Journal of Supercritical Fluids 52 (2010) pp. 306-316.

Kompella et al., "Recent Advances in Ophthalmic Drug Delivery", NIH Public Access, Author Manuscript Sep. 1, 2010, pp. 435-456.

Callegan et al., "Ocular Drug Delivery: a Comparison of Transcorneal Iontophoresis to Corneal Collagen Shields" International Journal of Pharmaceutics 123 (1995) pp. 173-179.

Myles et al., "Recent Progress in Ocular Drug Delivery for Posterior Segment Disease: Emphasis on Transcleral Iontophoresis" Advanced Drug Delivery Reviews 57 (2005) pp. 2063-2079.

The International Bureau of WIPO, International Preliminary Report on Patentability, International Application No. PCT/US2016/014636, 15 pages, dated Jul. 25, 2017.

* cited by examiner

IONTOPHORETIC CONTACT LENS

FIELD OF THE INVENTION

The present invention relates to improved methods and apparatus for delivering therapeutic compounds via ocular iontophoresis at a high ionization state, while maintaining physiologically acceptable conditions.

BACKGROUND

Ocular iontophoresis typically involves the application of an electrical source to propel charged and/or active molecules from a reservoir into the intraocular tissues of a mammal, including a human or an animal. Positively charged ions can be driven into the ocular tissues by electro-repulsion at the anode while negatively charged ions are repelled from the cathode. The simplicity and safety of iontophoretic application includes enhanced targeted delivery of compound(s) of interest, and the reduction of adverse side effects have resulted in extensive use of iontophoresis in laboratory, clinical research and commercial use.

Unlike ocular injections (intravitreal, retrobulbar, subconjunctival and peribulbar) and intraocular implants, iontophoresis is a noninvasive technique used to deliver compounds of interest into the anterior and/or posterior compartments of the eye. Iontophoretic delivery can be used to obtain intraocular concentrations and residence times that are equal to or greater than those achieved by conventional modalities such as topical drops, ointments, and gels.

Iontophoresis has been widely used in dermal applications in which therapeutic compounds are transported across a patient's skin using electrical currents. Due to the relative high impedance of the skin, the electrical currents are generally relatively low. Consequently, dosage times tend to be relatively long, for example being greater than an hour. In such applications, iontophoresis can be applied to the patient's skin with an active drug-containing adhesive patch.

Ocular iontophoresis devices are typically constituted by a direct current (DC) electric field source coupled to two electrodes, referred to respectively as "active" and "passive" electrodes. The active electrode provides an electromotive force, when energized, that acts on an electrolyte containing therapeutic composition(s) to transfer one or more therapeutic composition(s) across a surface of the eyeball, while the passive electrode serves as a return electrode and enables the electric circuit to be looped through the patient's body. The compound of interest is transported via the active electrode across the tissue when a current is applied to the electrodes through the tissue. Compound transport may occur as a result of a direct electrical field effect (e.g., electrorepulsion), an indirect electrical field effect resulted from the bulk volume flow of solution from the anode to cathode (e.g., electro-osmosis), electrically induced pore or transport pathway formation (e.g., electroporation), or a combination of any of the foregoing. Examples of currently known iontophoretic devices and methods for ocular drug delivery may be found in the U.S. Pat. Nos. 7,164,943; 6,697,668; 6,319,240; 6,539,251; 6,579,276; 6,697,668, and PCT publications WO 03/030989 and WO 03/043689, each of which is incorporated herein by reference.

Ocular iontophoresis, however, presents several unique challenges. For example, the applicator must conform to the spheroidal geometry of the eyeball. That is, the portion of the applicator in contact with a surface of the eye must be specifically formed to minimize loss of therapeutic composition and to reduce discomfort. Also, since the electrical impedance of the eye is relatively lower than that of the epidermis, higher currents can be achieved at still reasonably low current densities. Accordingly, dosage times tend to be relatively short, often much less than one hour.

Furthermore, iontophoretic transfer of a therapeutic composition with an inert electrode may result in unwanted changes in pH that result in patient discomfort, and in some instances, tissue damage. There remains a need to regulate the pH of a therapeutic preparation within the physiologically acceptable range during iontophoresis while maintaining the therapeutic composition at the highest ionization state for optimal delivery. Further, there remains a need to improve the delivery efficiency of a therapeutic composition while reducing the risks of any possible damage (e.g., irritation or burning of tissues) that could limit the use of ocular iontophoresis.

BRIEF SUMMARY

The present technology is related to devices and methods for ocular iontophoretic delivery of therapeutic compounds in safe and efficient manners.

One implementation provides a contact lens for ocular iontophoretic therapy. Such a contact lens may include a reservoir adapted to contain a charged therapeutic compound in an aqueous solution, wherein the reservoir may comprise a cavity within a layer of the contact lens, an absorption region (e.g., a porous structure or gel, etc.) within the layer, or other storage mechanism. Disposed on or within the contact lens may be a current source for providing iontophoretic current to the aqueous therapeutic compound solution and effecting a repulsive electromotive migration of the charged therapeutic compound into an ocular globe. The application of iontophoretic current may result, for inert electrodes, in the release of $OH^-$ or $H^+$ ions that, in addition to causing the electromotive repulsion, changes the pH of the aqueous compound solution. Also disposed on or within the contact lens may be a sensing circuit including a pH sensor for sensing whether the pH of the therapeutic compound solution is within a physiologically acceptable range, and a controller for controlling the current source, so as to permit the current to be adjusted and/or shut off, thereby enabling efficient delivery of the therapeutic compound while avoiding pH ranges potentially causing patient discomfort and/or injury.

In certain alternative embodiments, a voltage source supplying a voltage to an active sacrificial electrode in contact with the charged therapeutic compound may be disposed on or within the contact lens. The active electrode and a counter electrode may be coupled to opposite poles of the voltage source (e.g., a battery, etc.) The active sacrificial electrode may further comprise a sacrificial element or compound, for example silver or silver chloride. The active electrode may comprise an electrically conductive layer arranged to receive the current suitable for a chemical reduction-oxidation reaction sufficiently to create a release of ions. The release of the ions, which may be selected to have a polarity repulsive to the therapeutic compound, provides an electromotive force for driving the compound into the ocular tissue. A sensing circuit may be disposed on or within the contact lens, for measuring the conductivity of the active sacrificial electrode, and for controlling the current source and, thus, ion release and delivery of the therapeutic compound into the eyeball.

The contact lens may be comprised of one or more layers. In one implementation, the compound, inert or active electrodes, and current or voltage sources may be included in a single layer. A buffer adapted to maintain a selected pH range of the compound may also be included in this layer, or may be disposed in a distinct buffer layer.

In another embodiment, the contact lens may be comprised of a first conductive layer within or on which the electrode is disposed. Iontophoretic current or ions of repulsive polarity may be distributed to one or more layers including the compound and a buffer.

In yet another embodiment, the contact lens may be comprised of a first conductive layer including the current source and a second conductive layer having a higher resistivity than the first conductive layer, the second conductive layer adapted to evenly distribute current to at least one layer including the reservoir and buffer.

The contact lens may have a center portion to which the reservoir and other components may be annularly mounted. Contact lens layers may be fabricated according to techniques known in the relevant art, such as extrusion and lathe cutting, hydrogel molding, three dimensional printing, and other manufacturing techniques. The center portion may have a surface conforming to the shape of a corneal surface. The center portion may be inactive or active (e.g., for corneal drug delivery), in one or more of the electrodes, compound, buffer and circuitry may be disposed in the center portion, or they may be disposed in regions of the contact lens outside of the center portion.

The contact lens may be include a circuit including an iontophoretic current source including a power source that may comprise a stored energy component (e.g., a battery) or a power converter for wirelessly receiving energy (e.g., RF, solar, etc.) from an external power supply.

The circuit may also include sensing circuitry, including a pH sensor configured to detect the pH level of the charged therapeutic composition, and a controller for controlling the iontophoretic current source. A pH range of 4-8 is typically considered to be a physiologically acceptable pH range for aqueous compounds contacting an eyeball. If the sensing circuitry detects a pH level outside of this range, the controller may shut off the current to halt further deviation of the pH from the acceptable range. The controller may also be employed to maintain a selected therapeutic compound delivery rate, by adjusting the iontophoretic current supplied based on feedback from the pH sensor.

Certain implementations of the contact lens may include a material with a permanent charge and a selected polarity surrounding each reservoir in entirety or partially creating a barrier region 117a, 117b (such as shown in FIG. 1C.) The polarity of the permanently charged material will be the same charge as the electrode in the corresponding reservoir. The charged material will be in direct contact with the ocular surface to repel the charged ions exiting the reservoir(s) from traveling along the surface of the eye.

BRIEF DESCRIPTION OF THE DRAWING

The foregoing and other objects, features and advantages will be apparent from the following more particular description of the embodiments, as illustrated in the accompanying drawings in which like reference characters refer to the same parts throughout the different views. The drawings are not necessarily drawn to scale, emphasis instead being placed upon illustrating the principles of the embodiments.

DETAILED DESCRIPTION

Figure 1A:
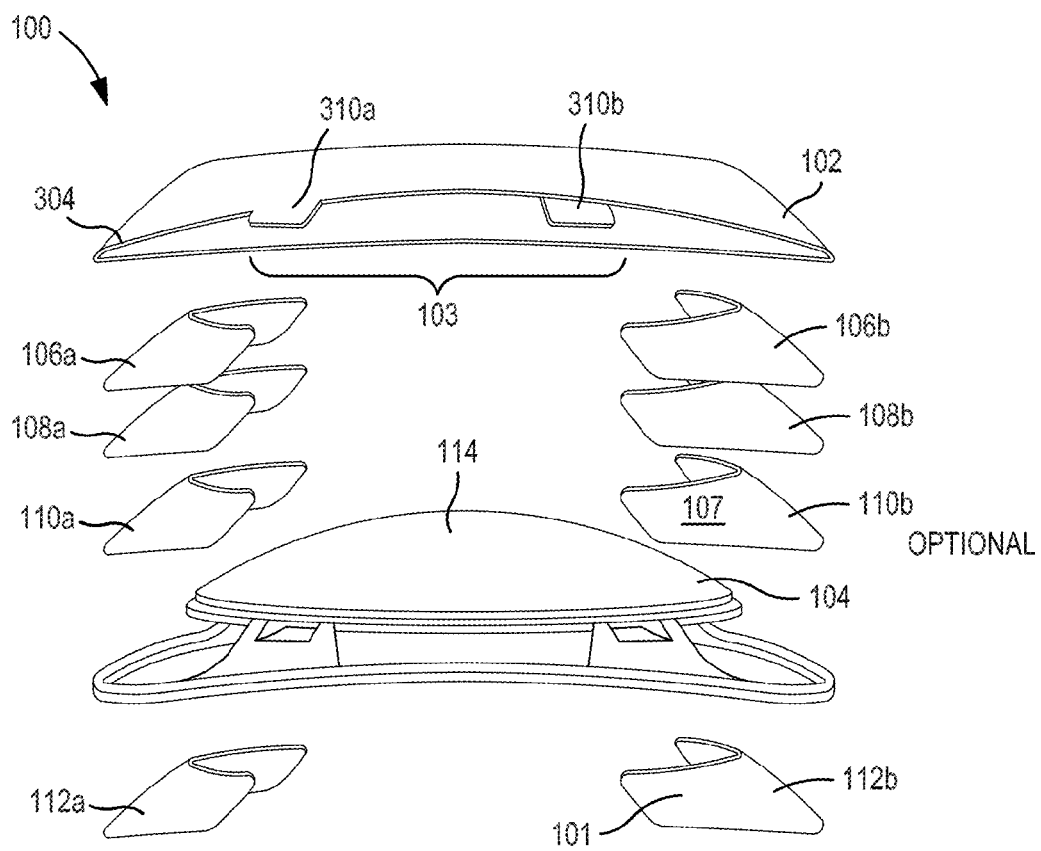
FIGS. 1A to 1C are exploded, cross-sectional and bottom views of a contact lens implementation.

It will be apparent to those skilled in the art in the view of this disclosure that modifications, substitutions and/or changes may be made without departing from the scope and spirit of the invention. In the description that follows, like components have been given the same reference numerals, regardless of whether they are shown in different examples. To illustrate an example(s) of the present disclosure in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

Ocular iontophoresis typically uses at least two electrodes (e.g., active and return, inactive or indifferent) to complete an electrical circuit, and when direct current is applied to the electrodes, ions of a polarity the same as the applied current are generated. These ions are used to repel like charged therapeutic compounds so as to be transported into the eye tissue. Compound transport may occur as a result of a direct electrical field effect (e.g., electrorepulsion), an indirect electrical field effect (e.g., electroosmosis), electrically induced pore or transport pathway formation (electroporation), or a combination of any of the foregoing. Examples of currently known iontophoretic devices and methods for ocular drug delivery may be found in U.S. Pat. Nos. 9,238,131, 9,192,512, 9,180,292, 9,149,525, 8,611,994, and 8,306,613, each of which is incorporated herein by reference.

Inert Electrode Embodiments

Figure 1B:
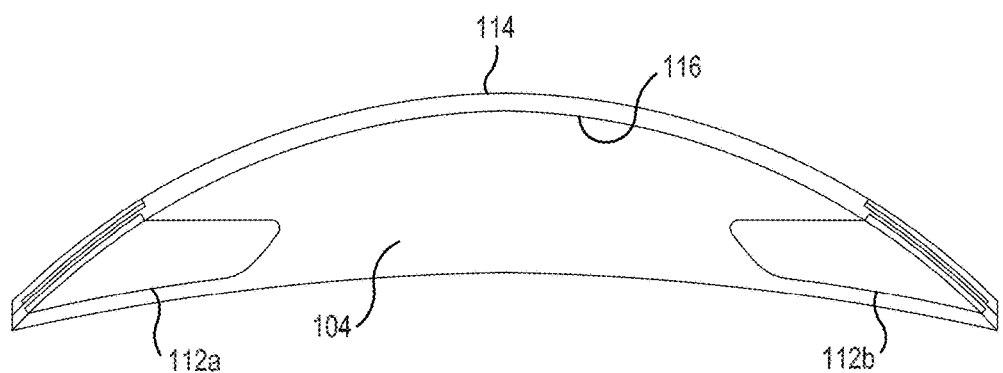
Figure 1C:
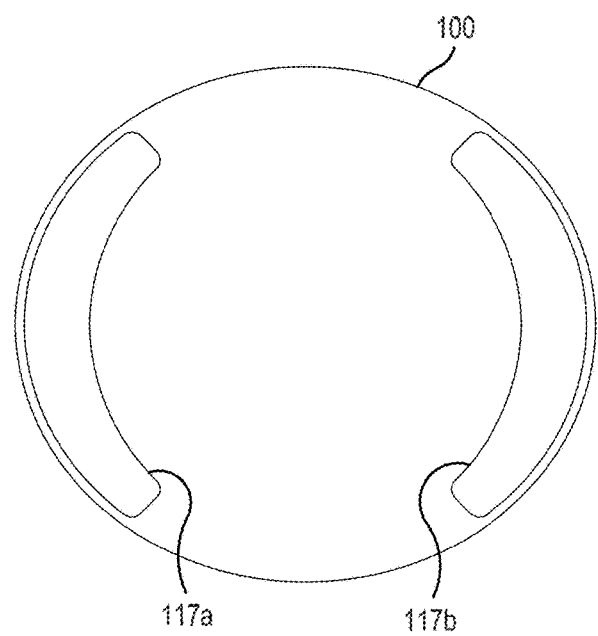
Figure 2:
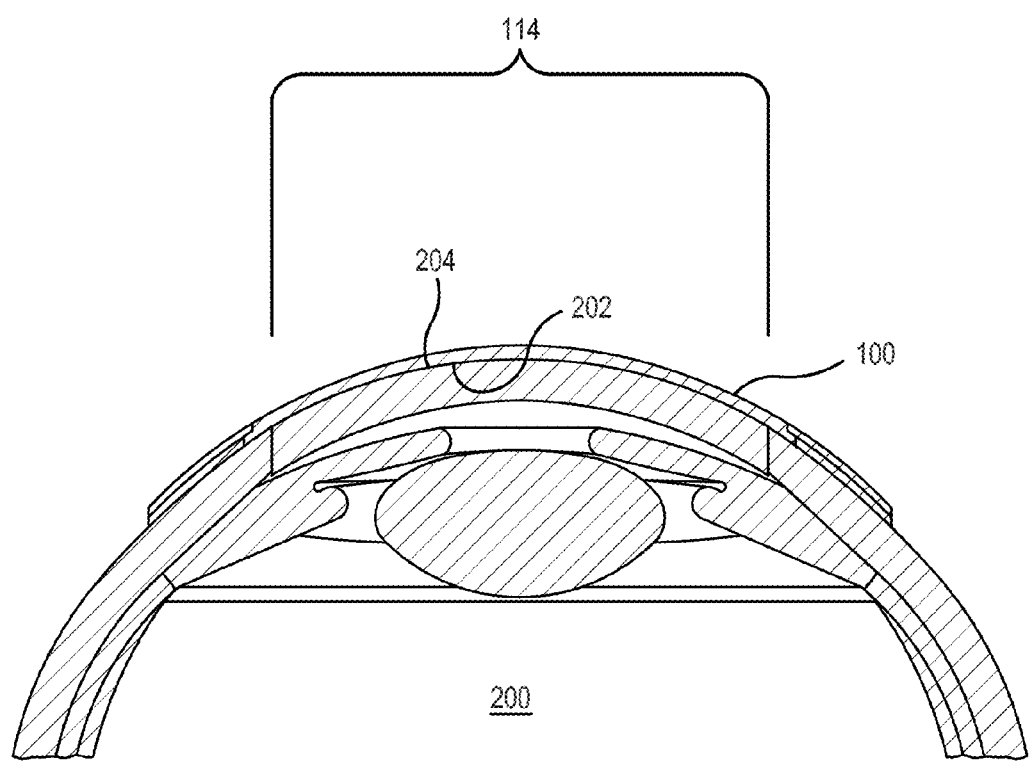
FIG. 2 is an illustration of an eyeball in contact with an iontophoretic contact lens embodiment.

FIGS. 1A-1C illustrate exploded, cross-sectional and bottom views, respectively, of an embodiment of a contact lens 100 configured for safe and effective deliver of therapeutic compounds 101 by ocular iontophoresis. In this embodiment, contact lens 100 is comprised of an annular top layer 102 having disposed therein or thereon an electrical circuit 103, a first conductive layer (shown as two annular electrodes 106a, 106b), a second conductive layer (shown as two annular electrodes 108a, 108b), optionally at least one buffer reservoir 110a, 110b, a tissue-contacting structural layer 104 configured to retain at least one charged therapeutic compound reservoir (actually illustrated as two compound reservoirs 112a, 112b). The contact lens 100 may be shaped as oval or generally round convex disc having a center portion 114 about which the various layers may be disposed, and dimensioned to fit over a corneal and scleral surface of an eye 200 (as shown in FIG. 2.) For an adult (nominal diameter of the cornea being approximately 12 mm), the internal diameter of the annular layers may be between 12.5 mm and 14 mm, while the outer diameter may be between 16 mm and 22 mm. Contact lens 100 may be formed from known biocompatible materials similar to those used in cosmetic contact lenses, such as polymeric materials, polyethylene terephthalate ("PET"), polymethyl methacrylate ("PMMA"), polyhydroxyethylmethacrylate ("polyHEMA"), a hydrogel, silicon based polymers (e.g., fluorosilicon acrylate), and/or combinations of these. Contact lens layers may be fabricated according to techniques known in the relevant art, such as extrusion and lathe cutting, three dimensional printing, and other manufacturing techniques.

Various types of therapeutic compounds may be used, depending on the type of medical procedure which is to be performed. For example, anesthetics such as lidocaine, antibodies, such as Vascular Endothelial Growth Factors or VEGF inhibitors, antibiotics, corticosteroids, antihistamines, tropicamide, or oligonucleotides may each be delivered iontophoretically as desired.

The compound reservoir 112a, 112b are illustrated as cavities within the tissue contacting structural layer 104 containing an electrically conductive aqueous solution or hydrogel capable of conducting the current and electric field supplied by the first conductive layer 102.

The optional buffer reservoir 110a, 110b contain a buffer 107 that may neutralize and maintain a physiologically acceptable range. A pH range of 3-8 is typically considered to be a physiologically acceptable pH range for aqueous compounds contacting an eyeball. Embodiments of suitable buffers 107 include, but are not limited to, those described in U.S. Pat. No. 9,180,292, already incorporated by reference above.

First conductive layer electrodes 106a,106b and second conductive layer electrodes 108a,108b apply a current to the aqueous solution in the buffer and/or reservoir layer causing an electrolysis reaction resulting in production of charged ions used to electro-repel charged therapeutic compound 101 across the surface of the eye. Three principle forces govern the flux caused by the current. The primary force is electrochemical repulsion, which propels like charged species through surfaces (tissues). When an electric current passes through an aqueous solution containing electrolytes and a charged material (for example, the charged pharmaceutical ingredient), several events occur: (1) the electrodes generates ions, (2) the newly generated ions approach/collide with like charged particles (typically the drug being delivered), and (3) the electrorepulsion between the newly generated ions force the dissolved/suspended charged particles into and/or through the surface adjacent (tissue) to the electrode. Continuous application of electrical current drives the charged compound significantly further into the tissues than is achieved with simple topical administration. The degree of iontophoresis is proportional to the applied current and the treatment time. Corticosteroids can be delivered at fixed or variable current settings ranging from, for example, about 0.1 mA to about 10 mA. The overall iontophoretic dose is a function of current and time. The iontophoretic dose, for example, can be applied over a period of less than about 10 minutes, less than about 15 minutes, less than about 20 minutes, or about 5 minutes.

Iontophoresis occurs in water-based preparations, where ions can be readily generated by electrodes. Two types of electrodes can be used to produce ions: (1) inert electrodes and (2) active electrodes. Each type of electrode requires aqueous media containing electrolytes. Iontophoresis with an inert electrode is governed by the extent of water electrolysis that an applied current can produce. The electrolysis reaction yields either hydroxide (cathodic) or hydronium (anodic) ions. Some formulations contain buffers, which can mitigate pH shifts caused by these ions. The presence of certain buffers introduces like charged ions that can compete with the drug product for ions generated electrolytically, which can decrease delivery of the drug product. The electrical polarity of the drug delivery electrode is dependent on the chemical nature of the drug product, specifically its pKa(s)/isoelectric point and the initial dosing solution pH. It is primarily the electrochemical repulsion between the ions generated via electrolysis and the drug product's charge that drives the drug product into tissues. Thus, iontophoresis offers a significant advantage over topical drug application, in that it increases drug absorption. The rate of drug delivery may be adjusted by varying the applied current, as determined by one of skill in the art.

First conductive layer electrodes 106a, 106b and second conductive layer electrodes 108a,108b may distribute current evenly, owing to their corresponding annular shapes, to the buffer reservoir 110a, 110b and compound reservoir 112a, 112b. The second conductive layer electrodes 108a, 108b may possess a higher resistivity than the first conductive layer electrodes 106a,106b and may be inert. This further ensures even current distribution to the buffer 107 without chemically reacting with the layer materials.

The layer(s) of contact lens 100 may be annularly mounted about an optic zone such as the center portion 114. When delivery of therapeutic compounds to the cornea is not desired, the center of the contact lens may be configured to be non-active. The center portion 114 may have a surface 202 conforming to the shape of a corneal surface 204 (as shown in FIG. 2.)

One or more of the therapeutic compound 101, buffer 107 and electrical circuit 103 may be disposed in annular regions of the contact lens 100 outside of the center portion 114. In alternative embodiments, center portion 114 may be omitted and the conductive, buffer, and reservoir layers may extend into the region of the center portion. In further embodiments, the electrical circuit 103, buffer reservoir 110a,110b, and compound reservoir 112a,112b may be positioned in the center portion 114, rather than annularly, i.e., when delivery of the therapeutic compound to the cornea or the entire ocular surface is desired.

Implementations of the contact lens 100 may include one or more barrier material regions 117a, 117b with permanent charge and a selected polarity surrounding each reservoir entirely or partially. The polarity of the permanently charged material will be the same charge as the electrode in the corresponding reservoir. The charged material will be in direct contact with the ocular surface to repel the charged ions exiting the reservoir(s) from traveling along the surface of the eye. Beneficially, this functionality may improve drug transport efficiency by minimizing loss of the therapeutic compound 101 and directing the therapeutic compound to the interior segment of the eye.

Figure 3:
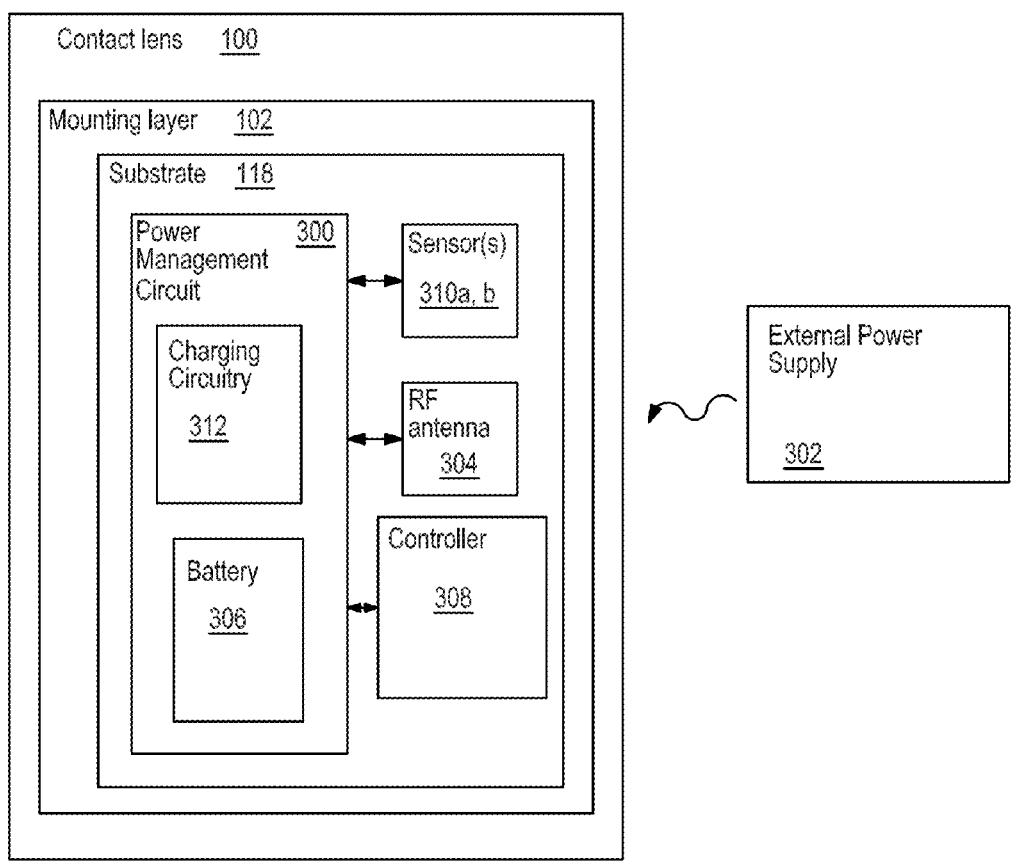
FIG. 3 is a block diagram of functional components of an iontophoretic contact lens system, including an external power supply.

With continued reference to FIG. 1A and additional reference to FIG. 3, electrical circuit 103 may be integrated in or on the annular mounting layer 102, and may include numerous functional components. Techniques are known to those of ordinary skill in the art for forming integrated circuits on or within a contact lens, such as described in U.S. Pat. Nos. 7,809,417, 8,755,880, 8,857,983, and 9,054,079, and U.S. Patent Pub. No. 2015/0305929, each of which is incorporated herein by reference in their entirety.

In various embodiments, circuit 103 may include any suitable circuit board substrate 118 attached to the mounting layer 102 by any suitable means, and to which one or more electronic components may be mounted, including a power management circuit 300 that may provide a pure AC signal, a pure DC signal, or an AC signal with a DC offset (depending on desired iontophoretic mode of action) to the first conductive layer electrodes 106a, 106b that may be in contact with the charged therapeutic compound 101. The electrodes in contact with the ocular surface may form a closed loop providing iontophoretic current to the charged therapeutic compound 101, buffer 107 and eye 200.

Power management circuit 300 may be configured with one or more stored energy components (e.g., a non-rechargeable battery, rechargeable battery 306, capacitor, etc.), and/or components for wirelessly receiving energy from an external energy source 302 and converting the received energy into a form for feeding the electrodes. One energy receiving means comprises a single turn loop RF antenna 304 connected to or mounted to the power management circuit 300 by any suitable means (e.g., solder, wirebond, conductive epoxy, conductive polymer, etc.) and positioned around the perimeter of mounting layer 102 so as to not interfere with the operation or structure of contact lens 100. The single-turn RF antenna 304 may be formed from any number of suitable conductive materials (e.g., copper, silver, gold, nickel, indium tin oxide, platinum, etc.) and constructed utilizing any number of techniques. Additionally, or alternatively, other energy receiving means could be employed, such as mechanical transducers and/or one or more photovoltaic cells, capturing light energy in the ultraviolet, visible and/or infrared bandwidths. Battery 306X may provide power to the various electronic components of power management circuit 300, and to a controller 308. Battery 306 may be inductively charged by a charging circuit 310 and energy harvesting RF antenna 304. Charging circuitry 310 may include a rectifier/regulator functioning to convert the received energy into DC, AC, and combinations thereof, to condition the captured energy for charging battery 306, or directly power controller 308 without battery 306.

In one embodiment, the external energy source 302 may be in the form of a conductive patch placed over a closed eyelid. The patch may be shaped to fit at least a portion of a closed eyelid. In alternative embodiments where it is preferred that the patient's eyes be open during treatment, the external energy source 302 may be any suitable wireless electrical source, such as an inductive energy source, resonant induction source, and radiofrequency (RF) energy source.

Figure 4:
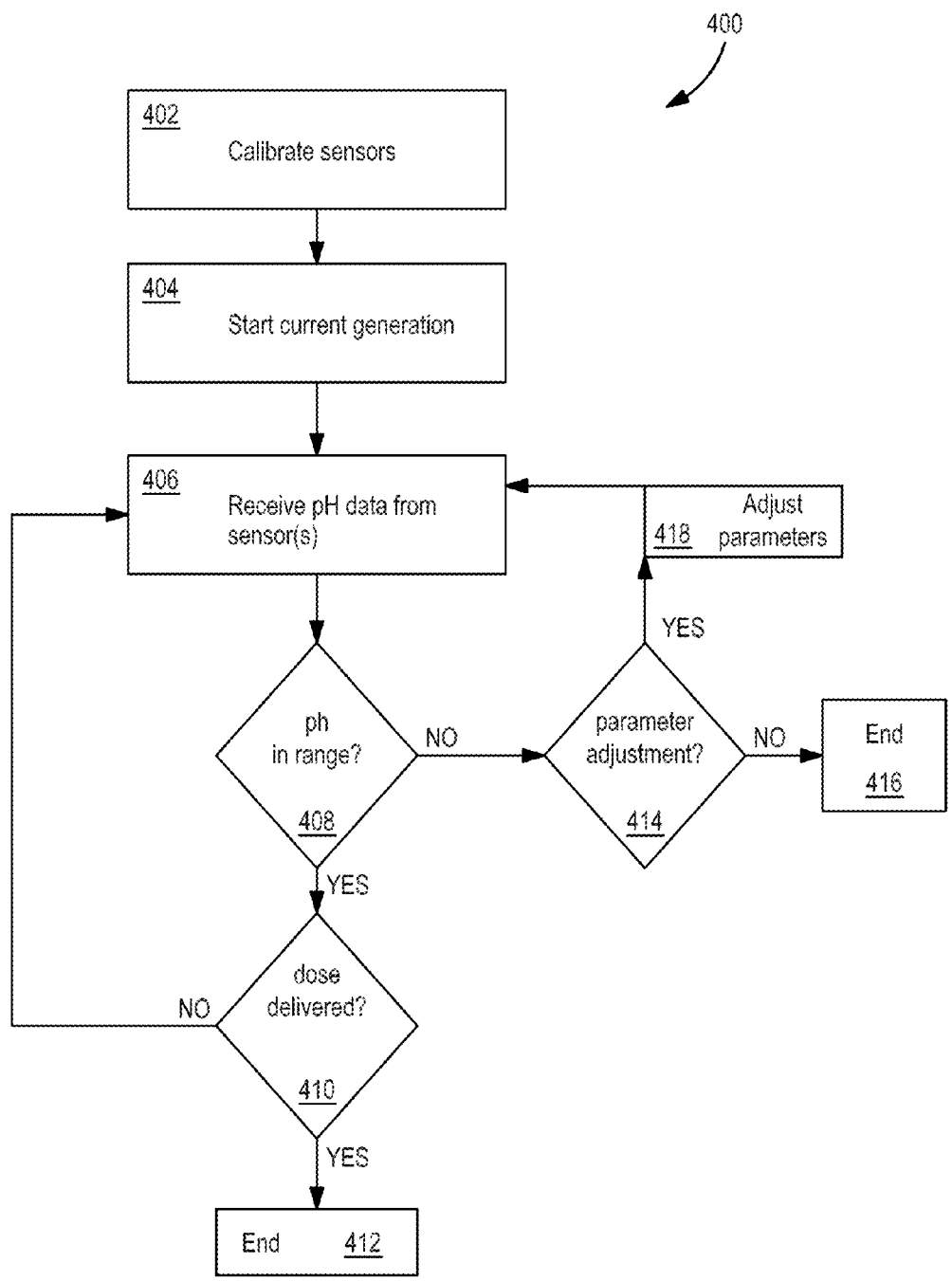
FIG. 4 is a logic flow diagram of a iontophoretic contact lens controller implementation.

Controller 308, comprising a microprocessor or internal state machine, may be configured to receive pH data from one or more pH sensors 310a, 310b configured to contact one or more of the surface of the eye 200, buffer reservoir 110a, 110b and compound reservoir 112a, 112b and to indicate the instant pH level of the aqueous solution including the charged therapeutic compound 101 (and preferably buffer 107.) FIG. 4 illustrates an example logic process 400 that may be followed by controller 308. In step 402, the pH sensors 310a, 310b may be initially calibrated to the normal pH. The drug delivery process may be started in step 404 with control signals to the power management circuit 300 to commence iontophoretic current generation. The application of iontophoretic current may result, for inert electrodes, in the release of OH⁻ or H⁺ ions that may change the pH of the aqueous compound solution. In step 406, the controller 308 receives pH data from the pH sensor(s) 310a, 310b. In step 408, controller 308 determines whether the measured pH level is maintaining a physiologically acceptable range (e.g., 3 to 8.) If the pH level is determined to be within the selected range, controller 308 in step 410 determines whether the desired drug dosage has been delivered. If so, controller 308 halts the process (in step 412) with control signals sent to power management circuit 300. If the complete dose has not yet been delivered, the process continues and monitoring continues by receiving a new set of pH data in step 406. If the pH level is determined to be out of the selected range in step 408, controller 308 determines in step 414 whether adjustments to the operating parameters of the power management circuit can affect iontophoretic current generation so as to bring the pH level back into the selected range. If not, controller 308 may provide control signals to other components of the power management circuit 300 that may cease operation (e.g., by halting battery charging, switching off power delivery etc.) Beneficially, in this manner, patient discomfort and eye damage may be avoided. In step 414, controller 308 may also determine that greater iontophoretic current and greater compound delivery rate is possible without exceeding the selected pH range, and send control signals to effect the higher delivery rate (step 418) before processing returns to pH monitoring step 406.

Sacrificial Electrode Embodiments

In a slightly different embodiment of the contact lens described above, ions of repulsive polarity may be employed to establish migration of ionic species of the therapeutic compound into the eye tissue from the contact lens. In such an embodiment, a first electrode may comprise a biocompatible active, sacrificial electrode suitable for use in contact with an eye. The active electrode element may include a sacrificial element such as a chemical compound including silver (Ag) or silver chloride (AgCl). Principles involved in active, sacrificial electrode iontophoresis are known, for example see U.S. Pat. No. 8,306,613, incorporated herein by reference in its entirety. So configured, the first electrode may be slowly consumed by contributing counter-ions to buffer the therapeutic composition. Examples include, but are not limited to, reactive conductive components (e.g., functionalized graphene, etc.)

In such implementations, the controller, rather than receiving pH data, may receive conductivity or resistivity data from electrode sensors monitoring the sacrificial electrode, and make similar determinations regarding operation of the power supplied to the electrodes based on the conductivity or resistivity data. The controller and power management circuit are similarly designed to deliver a constant current, requiring a certain electromotive force (voltage) to deliver that current. The sensors and/or controller monitor that voltage, which is then translated into a measure of resistivity. Once the resistivity increases to a level indicating that the sacrificial electrode is spent or close thereto, the controller will shut the system down. The active sacrificial electrode may comprise a sacrificial element or compound, for example silver or silver chloride. The active electrode may comprise an electrically conductive layer arranged to receive the current suitable for polarizing it sufficiently to electrolyze the therapeutic compound in solution. Ions released from ions the electrode, which may be selected to have a polarity repulsive to the therapeutic compound, provides an electromotive force for driving the compound into the ocular tissue.

Those of ordinary skill in the art will appreciate that functions of the components described above may be combined to simplify the design of the device. For example, in some implementations, the charged compound, electrodes, and current or voltage sources may be included in a single layer. A buffer adapted to maintain a selected pH range of the compound may also be included in this layer, or may be disposed in a distinct buffer layer.

The terms "comprise," "include," and/or plural forms of each are open ended and include the listed parts and can include additional parts that are not listed. The term "and/or" is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A contact lens for ocular therapy, comprising:
a reservoir containing a charged therapeutic composition;
a current source providing iontophoretic current to the charged therapeutic composition to affect delivery of the charged therapeutic composition into an eyeball;
a sensing circuit controlling the current source to maintain a selected pH range of the charged therapeutic composition; and
a polarity selective barrier region disposed at a perimeter of the reservoir and having a polarity the same as that of the charged composition in the corresponding reservoir.

2. The contact lens of claim 1, further comprising at least one of the following components:
a buffer layer adapted to maintain a selected pH range of the charged therapeutic composition within the reservoir;
a first conductive layer adapted to distribute the iontophoretic current to at least one of the reservoir and a buffer layer; and
a first conductive layer including the current source and a second conductive layer having a higher resistivity than the first conductive layer, the second conductive layer adapted to evenly distribute current to at least one of the reservoir and a buffer layer.

3. The contact lens of claim 2 further comprising a center portion to which the reservoir and the layer component(s) are annularly mounted.

4. The contact lens of claim 3, wherein the center portion has a surface conforming to a cornea surface.

5. The contact lens of claim 3, wherein the charged therapeutic composition, the current source and the sensing circuit are located outside of the center portion.

6. The contact lens of claim 1, comprising a layer having a surface conforming to a surface of an eyeball.

7. The contact lens of claim 1, wherein the current source comprises a power converter for receiving energy from an external source and converting the energy to the iontophoretic current.

8. A contact lens for ocular therapy, comprising:
a reservoir containing a charged therapeutic composition;
a current source providing iontophoretic current to the charred therapeutic composition to affect delivery of the charred therapeutic composition into an eyeball; and
a sensing circuit controlling the current source to maintain a selected pH range of the charged therapeutic composition,
wherein the sensing circuit comprises:
a pH sensor configured to detect the pH level of the charge therapeutic composition; and
a current source controller configured to change the iontophoretic current when the detected pH level is outside the selected pH range
a polarity selective barrier region disposed at a perimeter of the reservoir having a polarity the same as that of the charged composition in the corresponding reservoir.

9. The contact lens of claim 1, wherein the current source comprises a converter configured to convert power wirelessly received from an external source.

10. The contact lens of claim 1, wherein the current source comprises at least one of an energy storage component and energy harvesting circuitry.

11. A contact lens for ocular therapy, comprising:
a reservoir adapted to contain a charged therapeutic compound;
a sacrificial electrode with a sacrificial element in contact with the charged therapeutic compound, the sacrificial electrode adapted to generate ions having the same charge polarity as the charged therapeutic compound through consuming the sacrificial element;
a voltage source providing iontophoretic voltage to the sacrificial electrode to affect an electric motive force causing delivery of the charged therapeutic compound into an eyeball; and
a sensing circuit controlling the voltage source to adjust the delivery of the charged therapeutic compound.

12. The contact lens of claim 11 wherein:
the sensing circuit comprises
a sensor configured to detect the conductivity of the sacrificial electrode, and
a voltage source controller configured to change the iontophoretic voltage when the detected sacrificial electrode conductivity is outside a selected range.

* * * * *